US008211469B2

(12) United States Patent
Dieckmann et al.

(10) Patent No.: US 8,211,469 B2
(45) Date of Patent: Jul. 3, 2012

(54) USE OF BLOCK COPOLYMERS BASED ON VINYLLACTAMS AND VINYL ACETATE AS SOLUBILIZERS

(75) Inventors: Yvonne Dieckmann, Haβloch (DE);
Murat Mertoglu, Ludwigshafen (DE);
Rainer Dobrawa, Mannheim (DE);
Szilard Csihony, Weinheim (DE);
Cedric Dieleman, Scheibenhard (FR);
Torsten Knieriem, Mannheim (DE);
Sebastian Koltzenburg,
Dannstadt-Schauernheim (DE); Holger Türk, Mannheim (DE); Ulrike Troppmann, Mannheim (DE);
Christian Michael Jung, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 299 days.

(21) Appl. No.: 12/514,078

(22) PCT Filed: Oct. 31, 2007

(86) PCT No.: PCT/EP2007/061759
§ 371 (c)(1),
(2), (4) Date: May 8, 2009

(87) PCT Pub. No.: WO2008/058848
PCT Pub. Date: May 22, 2008

(65) Prior Publication Data
US 2010/0047203 A1 Feb. 25, 2010

(30) Foreign Application Priority Data

Nov. 13, 2006 (EP) ..................................... 06123959
Dec. 5, 2006 (EP) ..................................... 06125423

(51) Int. Cl.
*A61K 9/14* (2006.01)
(52) U.S. Cl. ...................................................... 424/486
(58) Field of Classification Search ........................ None
See application file for complete search history.

(56) References Cited

U.S. PATENT DOCUMENTS

| 5,502,136 | A | 3/1996 | Zhong et al. |
| 5,900,247 | A | 5/1999 | Rault et al. |
| 6,075,107 | A | 6/2000 | Kothrade et al. |
| 6,153,705 | A | 11/2000 | Corpart et al. |
| 6,271,307 | B1 | 8/2001 | Huff et al. |
| 6,767,865 | B2 * | 7/2004 | Den Tandt et al. ............ 504/362 |
| 6,867,262 | B1 | 3/2005 | Angel et al. |
| 2002/0037318 | A1 | 3/2002 | Meffert et al. |
| 2007/0122436 | A1 | 5/2007 | Koltzenburg et al. |

FOREIGN PATENT DOCUMENTS

| DE | 1 245 542 | 7/1967 |
| DE | 19935063 | 2/2001 |
| EP | 0781550 | 7/1997 |
| EP | 991683 | 12/1997 |
| EP | 0876819 | 11/1998 |
| EP | 948957 | 10/1999 |
| EP | 0953347 | 11/1999 |
| EP | 1027886 | 8/2000 |
| EP | 1269994 | 1/2003 |
| EP | 1 510 533 | 3/2005 |
| WO | WO 98/01478 | 1/1998 |
| WO | WO 0053164 | 9/2000 |
| WO | WO 2004019901 | 3/2004 |
| WO | WO 2004035013 | 4/2004 |
| WO | WO 2005/046328 | 5/2005 |

OTHER PUBLICATIONS

International Search Report for International Application No. PCT/EP2007/061759; International Filing Date: Oct. 31, 2007; Date of Completion: Feb. 25, 2008; Date of Mailing: Mar. 6, 2008.
International Preliminary Report on Patentability for International Application No. PCT/EP2007/061759; International Filing Date: Oct. 31, 2007.
Bilalis et al., "Controlled nitroxide-mediated and reversible addition-fragmentation chain transfer polymerization of n-vinylpyrrolidone: Synthesis of block copolymers with styrene and 2-vinylpyridine", Journal of Polymer Science: Part A, 44, 659-665 (2006).
Nguyen, T.L. Uyen et al., "Investigation of the influence of the architectures of poly(vinyl pyrrolidone) polymers made via the reversible addition-fragmentation chain transfer/macromolecular design via the interchange of xanthates mechanism on the stabilization of suspension polymerizations", Journal of Polymer Science: Part A, 44, 4372-4383 (2006).
Römpp Chemie Lexikon, 9. Auflage, Bd. 5, S. 4203, Thieme Verlag, Stuttgart, 1992.

* cited by examiner

*Primary Examiner* — Paul Dickinson
(74) *Attorney, Agent, or Firm* — Brinks Hofer Gilson & Lione

(57) ABSTRACT

Use of polyvinyllactam-polyvinyl acetate block copolymers as solubilizers for active ingredients that are sparingly soluble in water.

14 Claims, No Drawings

USE OF BLOCK COPOLYMERS BASED ON VINYLLACTAMS AND VINYL ACETATE AS SOLUBILIZERS

This application is a National Stage application of International Application No. PCT/EP2007/061759 filed Oct. 31, 2007, the entire contents of which is hereby incorporated herein by reference. This application also claims the benefit under 35 U.S.C. §119 of European Patent Application No. 06123959.6, filed Nov. 13, 2006 and European Patent Application No. 06125423.1, filed Dec. 5, 2006, the entire contents of which is hereby incorporated herein by reference.

The present invention relates to the use of block copolymers based on vinyllactams and vinyl acetate as solubilizers and crystallization inhibitors for active ingredients that are sparingly soluble in water, in particular of pesticides (agrochemical active ingredients).

In the production of homogenous preparations in particular of biologically active substances, the solubilization of hydrophobic substances, i.e. substances that are sparingly soluble in water, has gained very great practical importance.

Solubilization is to be understood as meaning making substances that are insoluble or sparingly soluble in a certain solvent, in particular water, soluble through interface-active compounds, the solubilizers. Such solubilizers are able to convert sparingly water-soluble or water-insoluble substances into clear, at most opalescent, aqueous solutions without the chemical structure of these substances undergoing a change as a result (cf. Römpp Chemie Lexikon, 9th edition, vol. 5, p. 4203, Thieme Verlag, Stuttgart, 1992).

The solubilisates produced are characterized in that the sparingly water-soluble or water-insoluble substance is present in colloidally dissolved form in the molecular associations of the surface-active compounds which form in aqueous solution, such as, for example, hydrophobic domains or micelles. The resulting solutions are stable or metastable single-phase systems which appear optically clear to opalescent.

Solubilizers can, for example, improve the appearance of cosmetic formulations and of food preparations by making the formulations transparent. Furthermore, in the case of pharmaceutical preparations, the bioavailability and thus the effect of drugs can also be increased through the use of solubilizers.

The solubilizers used for pharmaceutical drugs and cosmetic active ingredients are preliminary surfactants such as ethoxylated *ricinus* oil or ethoxylated hydrogenated *ricinus* oil, ethoxylated sorbitan fatty acid esters or ethoxylated hydroxystearic acid.

The above-described solubilizers used hitherto, however, have a number of application-related disadvantages.

The known solubilizers have only a slight solubilizing effect for some sparingly soluble drugs, such as, for example, clotrimazole.

EP-A 876 819 describes the use of copolymers of at least 60% by weight of N-vinyl-pyrrolidone and amides or esters with long-chain alkyl groups.

EP-A 948 957 describes the use of copolymers of monoethylenically unsaturated carboxylic acids, such as, for example, acrylic acid, and hydrophobically modified comonomers, such as, for example, N-alkyl- or N,N-dialkylamides of unsaturated carboxylic acids with $C_8$-$C_{30}$-alkyl radicals.

DE-A 199 350 63 discloses graft polymers containing polyalkylene oxide on the basis of vinyllactams and vinyl acetate, and their use as gas hydrate inhibitors.

EP-A 953 347 discloses the use of graft polymers containing polyalkylene oxide as solubilizers. The graft polymers of vinyl acetate and polyalkylene oxides described therein often do not constitute powders, but viscous-sticky liquids, which is disadvantageous from the point of view of application.

EP 0781 550 discloses the use of random copolymers of vinylpyrrolidone and vinyl acetate as bioadhesion agents in pharmacy.

DE 1245542 discloses the use of random copolymers of polyvinylpyrrolidone with vinyl acetate as solvent for peptide antibiotics. The block copolymer specified is the block copolymer of polyoxyethylene and polyoxypropylene.

Numerous types of block polymers are prepared by ionic polymerization. However, this method is not suitable for all monomers. A polymerization via free-radically initiated methods is open to a large number of monomers, but a normal free-radical polymerization cannot be used for producing block copolymers.

For this reason, the method of controlled free-radical polymerization, which is also referred to as "living" polymerization, was developed.

One variant of living free-radical polymerization is the so-called "RAFT" method (RAFT: Reversible Addition-Fragmentation chain Transfer). Here, suitable chain transfer agents, which are also referred to as RAFT reagents, are certain sulfur compounds, for example dithiocarbamates or xanthates.

EP-B 991 683 describes the production of block copolymers from polyvinyl acetate and polyalkyl acrylate blocks via living polymerization with xanthates.

WO 98/01478 discloses the production of block polymers of polyalkyl acrylates and polystyrenes via living polymerization with thiocarbonylthio compounds as chain transfer agents.

EP-A 1510533 describes the production of block copolymers comprising polyvinyllactam blocks by living polymerization. The polyvinyllactam block here may also be a copolymer of vinyllactam and up to 45% by weight of vinyl acetate. The coblocks described are polyhydrocarbons or poly(meth)acrylates.

P. Bilalis et al., Journal of Polymer Science: Part A, Vol. 44, 659-665 (2006) discloses the production of polyvinylpyrrolidone block copolymers by means of RAFT polymerization.

T. L. Uyen Nguyen et al. describe in Journal of Polymer Science: Part A, Vol. 44, 4372-4383 (2006) the production of block copolymers of polyvinylpyrrolidone and polyvinyl acetate blocks by controlled polymerization, and the use of such block copolymers as stabilizers in the suspension polymerization of special crosslinked polymer microspheres.

A further desirable requirement of solubilizers is the ability to form so-called "solid solutions" with sparingly soluble substances. The term "solid solution" refers to a state in which a substance is distributed in microdisperse form or, in the ideal case, in molecularly disperse form, in a solid matrix, for example a polymer matrix. Such solid solutions lead, for example when used in solid pharmaceutical administration forms of a sparingly soluble active ingredient, to improved release of the active ingredient. An important requirement of such solid solutions is that they are also stable upon storage over an extended period, i.e. that the active ingredient does not crystallize out. Furthermore, the capacity of the solid solution, in other words the ability to form stable solid solutions with the highest possible active ingredient contents, is also of importance.

Solid solution here refers to a state in which the active ingredient is present in molecularly disperse distribution in a matrix of auxiliaries. In this state, crystalline fractions of the active ingredient can no longer be established by means of X-ray diffractometry. Since the detection limit for crystalline fractions in X-ray diffractometry is 3% by weight, the expression "no crystalline fractions" means that less than 3% by weight of crystalline fractions are present. The state of the molecularly disperse distribution can be ascertained with the help of the differential scanning calorimetry (DSC) method. In the case of a molecularly disperse distribution, a melting peak can no longer be observed in the region of the melting point of the active ingredient. The detection limit of this method is 1% by weight. WO 05/046328 gives examples of solid solutions.

For the formation of solid solutions, besides the fundamental ability of the solubilizers to form solid solutions, the hygroscopicity of the solubilizers also plays an important role. Solubilizers which absorb too much water from the ambient air lead to deliquescence of the solid solution and the undesired crystallization of the active ingredients. An extensively great hygroscopicity can also present problems during processing to give administration forms or solid agrochemical preparations.

Particularly in the case of agrochemical preparations, this can lead to problems during storage as a result of so-called agglutination.

The hitherto known polymeric solubilizers have the disadvantages that they do not form stable solid solutions. Furthermore, they still leave room for improvements regarding solubilization in aqueous systems. Some of the known solubilizers also have disadvantages with regard to processability on account of their tendency toward stickiness since they do not constitute adequately flowable powders.

Furthermore, particularly in the case of agrochemical preparations, it is of importance to achieve high storage stability of the preparation through selection of suitable solubilizers (e.g. by avoiding crystallization formation) and/or, through selection of a suitable solubilizer, to increase the bioavailability of the pesticide and/or have the lowest possible phytotoxicity. There is a constant need here to find suitable solubilizers.

In the case of the formulation of active ingredients that are sparingly soluble in water, there is the problem that the sparingly soluble active ingredient in the aqueous formulation has a tendency toward crystallization during storage. For sparingly soluble active ingredients, this problem is naturally closely related to the problem of lack of solubilization.

It was therefore the object to provide novel and improved solubilizers for pharmaceutical, cosmetic, food or agrochemical applications which do not have the described disadvantages. Moreover, it is an object of the present invention to provide solubilizers in particular for sparingly soluble pesticides which permit high storage stability of the agrochemical preparations and/or increase the bioavailability of the pesticide and/or have the lowest possible phytotoxicity.

As already explained, it was an object of the present invention to provide improved copolymers as solubilizers and as crystallization inhibitors.

Accordingly, the use of block copolymers consisting of at least one polyvinyllactam block and at least one polyvinyl acetate block as solubilizers for active ingredients that are sparingly soluble in water has been found. Furthermore, accordingly, the use of block copolymers consisting of at least one polyvinyllactam block and at least one polyvinyl acetate block as crystallization inhibitors for active ingredients that are sparingly soluble in water, preferably pesticides, has been found. Furthermore, it has been found that the block copolymers according to the invention can simultaneously solve the abovementioned problems of solubilization and of crystallization inhibition.

For the purposes of the present invention, active ingredients are understood as meaning biologically active substances which are used in pharmaceutical preparations or cosmetic preparations, food supplements or foods. They are also understood as meaning biologically active substances for agrochemical applications (also called pesticides or agrochemical active ingredients).

In particular, these block copolymers are suitable as solubilizers and/or crystallization inhibitors for pesticides that are sparingly soluble in water.

The block copolymers may be of the AB, ABA or BAB type.

Suitable as polyvinyllactam are N-vinylpyrrolidone, N-vinylpiperidone or N-vinylcaprolactam, preferably polyvinylpyrrolidone.

The molar ratio of polyvinyllactam to polyvinyl acetate (PVAc) can be 10 to 90 to 90 to 10, preferably 30 to 70 to 70 to 30, particularly preferably 60:40 to 40:60.

Hereinafter, the polyvinyllactam block is also referred to as A block, and the polyvinyl acetate block is referred to as B block.

In principle, the block copolymers can be prepared by any method suitable for this purpose.

Thus, for example, coupling of the PVP and the PVAc blocks can take place via diisocyanates.

In order to make it possible for the polyvinyl acetate block to couple onto the polyvinyllactam block, the polymer blocks are functionalized at the chain start and/or at the chain end with hydroxyl groups. The OH functionalization can be achieved either via the radical starter or via a regulator. Functionalization via the radical starter takes place at the chain start, functionalization via the regulator at the chain end. In order to achieve a functionalization, at least one radical starter carrying hydroxyl groups or one regulator carrying hydroxyl groups must therefore be used in the polymerization of the prepolymers. If B-A-B or A-B-A block copolymers are to be produced, radical starters and regulators must carry hydroxyl groups.

General methods of producing the vinyllactam prepolymers and the polyvinyl acetate prepolymers are known per se.

The production takes place by free-radically initiated polymerization in suitable solvents.

Suitable N-vinyllactams are N-vinylpyrrolidone, N-vinylcaprolactam or N-vinylpiperidone or mixtures thereof. Preference is given to using N-vinylpyrrolidone.

Suitable nonaqueous solvents are, for example, alcohols, such as methanol, ethanol, n-propanol, and isopropanol, and also glycols, such as ethylene glycol and glycerol.

Also suitable as solvents are acetic acid esters, such as, for example, ethyl acetate or butyl acetate.

Preference is given to using those solvents which do not act as regulator. These are known to the person skilled in the art.

For the solvents for producing the polyvinyl acetate, that stated above is applicable.

The polymerization is preferably carried out at temperatures from 60 to 100° C.

To initiate the polymerization, free-radical initiators are used as radical starters. The amounts of initiator or initiator mixtures used, based on monomer used, are between 0.01 and 10% by weight, preferably between 0.3 and 5% by weight.

Depending on the type of solvent used, both organic and inorganic peroxides are suitable, such as sodium persulfate or azo starters such as azobisisobutyronitrile, azobis(2-amidopropane) dihydrochloride or 2,2'-azobis(2-methylbutyronitrile).

Peroxidic initiators are, for example, dibenzoyl peroxide, diacetyl peroxide, succinyl peroxide, tert-butyl perpivalate, tert-butyl 2-ethylhexanoate, tert-butyl permaleinate, bis(tert-butylperoxy)cyclohexane, tert-butyl peroxyisopropylcarbonate, tert-butyl peracetate, 2,2-bis(tert-butylperoxy)butane, dicumyl peroxide, di-tert-amyl peroxide, di-tert-butyl peroxide, p-menthane hydroperoxide, pinane hydroperoxide, cumene hydroperoxide, tert-butyl hydroperoxide, hydrogen peroxide, and mixtures of the specified initiators. The specified initiators can also be used in combination with redox components such as ascorbic acid.

If the OH functionalization is to take place via the radical starter, OH-functionalized starters in particular are suitable, such as, for example, 2,2'-azobis[2-methyl-N-(2-hydroxyethyl)propionamide], 2,2'-azobis{2-methyl-N-[2-(1-hydroxybutyl)]propionamide} or 2,2'-azobis{2-[1-(2-hydroxyethyl)-2-imidazolin-2-yl]propane} dihydrochloride.

The free-radical polymerization can, if appropriate, take place in the presence of emulsifiers, if appropriate further protective colloids, if appropriate buffer systems and if appropriate subsequent pH adjustment by means of bases or acids.

Suitable molecular weight regulators are hydrogen sulfide compounds, such as alkyl mercaptans, e.g. n-dodecylmercaptan, tert-dodecyl mercaptan, thioglycolic acid and esters thereof, mercaptoalkanols such as mercaptoethanol. Further suitable regulators are specified, for example, in DE 197 12 247 A1, page 4. The required amount of molecular weight regulator is in the range from 0 to 5% by weight, based on the amount of monomers to be polymerized, in particular 0.05 to 2% by weight, particularly preferably 0.1 to 1.5% by weight. Preference is given to mercaptoethanol.

The monomers or a monomer mixture or the monomer(s) emulsion are initially introduced together with the initiator, which is usually in the form of a solution, in a stirred reactor at the polymerization temperature (batch process), or metered into the polymerization reactor if appropriate continuously or in a plurality of successive stages (feed method). In the case of the feed method, it is customary, before the start of the actual polymerization, for the reactor to already contain, besides water (in order to permit stirring of the reactor) part amounts, rarely the total amount intended for the polymerization, of the feed materials such as emulsifiers, protective colloids, monomers, regulators etc. or part amounts of the feeds (including monomer feed or emulsion feed and initiator feed).

The polyvinyl acetates are reacted in equimolar amounts, based on the hydroxyl groups in the polyvinyl acetate and in the vinyllactam prepolymer. The amount of OH groups present can, if required, be ascertained in a manner known per se to the person skilled in the art. To ascertain the hydroxyl number, see, for example, Römpp Chemie Lexikon, 9th edition, 1990.

The coupling of vinyllactam polymers and polyvinyl acetates takes place through reaction with diisocyanates, the reaction with the hydroxyl groups of the polymer resulting in coupling via urethane groups. In this connection, either the vinyllactam polymer or the polyvinyl acetate can firstly be reacted with the diisocyanate.

According to a preferred embodiment of the invention, the coupling takes place via polyvinyl acetates functionalized with isocyanate groups as end groups. For this, the polyvinyl acetate is firstly reacted with the diisocyanate and then the polyvinyl acetate functionalized in this way is reacted with the vinyllactam polymer.

Irrespective of which embodiment is selected, the reaction can take place as follows:

Suitable diisocyanates are compounds of the general formula OCN—R—NCO, where R may be aliphatic, alicyclic or aromatic radicals, which can also be substituted by alkyl radicals.

Suitable diisocyanates are preferably compounds whose isocyanate groups have varying reactivity, on account of the molecular structure, toward nucleophiles, for example isophorone diisocyanate or toluoylene diisocyanate.

Also suitable in principle are symmetrical diisocyanates, such as, for example, hexamethylene diisocyanate or 4,4'-methylenedi(phenyl isocyanate).

Preference is given to using isophorone diisocyanate.

The reaction with the diisocyanate preferably takes place in an organic solvent, such as ketones, for example acetone, furthermore dimethyl sulfoxide, dimethylformamide, or generally aprotic-polar organic solvents or mixtures of such solvents. The reaction usually takes place at elevated temperatures, the temperature also being governed by the boiling temperature of the selected solvent. The reaction of the diisocyanate with the first component can take place at 20 to 50° C., but also if desired up to 100° C. The reaction of the second isocyanate group can take place at temperatures from 50 to 100° C.

The reaction preferably takes place in equimolar amounts, which means that the quantitative ratio is selected such that, per mole of hydroxyl group to be reacted, 1 mol of diisocyanate is used. If the vinyllactam polymer is OH-functionalized via a regulator, the diisocyanate is reacted in equimolar amounts relative to the regulator. If the vinyllactam polymer is OH-functionalized via a radical starter, then 2 mol of diisocyanate are used per mole of radical starter.

In the case of symmetrical diisocyanates, it may also be advisable to use an excess of diisocyanate and then to remove the excess by distillation.

The reaction is preferably carried out in the presence of a catalyst. Suitable catalysts are, for example, organometallic compounds such as organotitanium compounds or zinc compounds, such as dibutyltin dilaurate or tin octoate, furthermore bases such as 1,4-diaza(2,2,2)bicyclooctane or tetramethylbutanediamine. The catalyst can be used in amounts of from 0.05 to 0.2 mol, preferably 0.1 to 0.14 mol, per mole of diisocyanate.

The reaction is usually carried out at elevated temperatures in the range from 50 to 100° C. Which temperature is selected specifically depends on the nature of the organic solvent used. The solvent can then be removed by distillation.

Usually, the reaction is carried out in such a way that firstly the component, which should be isocyanate-group-functionalized, is reacted with the diisocyanate in the presence of the catalyst and a solvent until the isocyanate value in the reaction mixture has dropped to half. This can be ascertained in a known manner, for example titrimetrically. The other component is then added, the amounts of isocyanate groups and OH or amino groups again being selected to be equimolar. The reaction is continued until the isocyanate value has dropped to zero.

The block copolymers are preferably prepared by a method, known per se, of controlled free-radical polymerization, which is also referred to as RAFT polymerization (Reversible Addition—Fragmentation chain Transfer). The mechanism of this method is described in detail in WO 98/01478 and EP-A 991 683, to the disclosure of which reference is hereby expressly made.

The RAFT polymerization takes place in the presence of specific chain transfer agents, also referred to as RAFT reagents, from the group of thiocarbonylthio compounds, in particular the dithiobenzoates, the trithiocarbonates, the dithiocarbamates and the dithiocarbonic acid esters, which are also referred to as xanthates. Such reagents are known to the person skilled in the art from the prior art. Thus, of suitability are, for example, the compounds described in WO 98/01478 or EP-A 991 683.

Preferred RAFT reagents are diphenyl dithiocarbamate of diethyl malonate and 2-(ethoxycarbonothioyl)thiopropionic acid.

To produce the block copolymer, the PVP block is firstly prepared by free-radically initiated solution polymerization by mixing N-vinyllactam, RAFT reagent and radical starter in a solvent and reacting them at elevated temperature.

Suitable radical starters are azo starters, such as 2,2'-azobis (2,4-dimethylvaleronitrile), dimethyl, azobisisobutyronitrile, dimethyl 2,2'-azobisisobutyrate, 1,1'-azobis(1-cyclo-hexanecarbonitrile), 2,2'-azobis(2-methylbutyronitrile) or 4,4'-azobis[2-methyl-N-(2-hydroxyethyl)propionamide], preferably azobisisobutyronitrile (AIBN). The radical starter can be used in amounts of from 5 to 50 mol %, preferably 5 to 15 mol %, based on RAFT reagent.

The vinyllactam monomers, RAFT reagents and radical starters can be used in molar ratios of from 350:2:1 (monomer:RAFT:starter) to 3500:10:1, preferably 1000:10:1 to 2000:10:1.

Suitable solvents are organic solvents which do not act as regulators, for example methanol, n-propanol, tert-butanol, dimethylformamide, ethyl acetate, butyl acetate or dioxane, preferably dioxane or tert-butanol.

The reaction can take place at temperatures of from 50 to 120° C., preferably 60 to 80° C.

When the polymerization is complete, it is advisable to treat the polyvinyllactam functionalized with RAFT reagent in such a way that any unreacted vinyllactam is removed. This can take place, for example, by precipitating the polymer out of the reaction mixture and removing it by filtration. The precipitation can take place, for example, by adding a nonsolvent. A suitable nonsolvent is primarily diethyl ether. Furthermore, the polymer can also be purified by acidic hydrolysis of the monomeric vinyllactam with subsequent removal of the resulting lactam by distillation.

The PVP block functionalized with the RAFT reagent is then reacted with vinyl acetate in the presence of a radical starter.

Suitable radical starters are the compounds described for the production of the polyvinyllactam block. The reaction can otherwise take place under the conditions described for the formation of the polyvinyllactam block.

When the polymerization is complete, the resulting block polymer can be worked-up in a manner customary per se, for example by separating off the solvent by distillation.

The block copolymers are preferably water-soluble, but may also be water-dispersible.

The molecular weights Mn may be 5000 to 50 000, preferably 10 000 to 30 000.

Applications:

The copolymers to be used according to the invention can in principle be used in all fields where active ingredients that are insoluble or only sparingly soluble in water are to be used for certain applications on people and animals or in the agrochemical sector either in aqueous preparations, or their effect is to develop in an aqueous medium.

According to the invention, the term "sparingly soluble in water" also comprises virtually insoluble substances and means that for a solution of the substance in water at 20° C., at least 30 to 100 g of water per g of substance is required. This means, for example, that at least 30 g, but in many cases also at least 100 g, of water is required per g of substance. In the case of virtually insoluble substances, at least 10 000 g of water are required per g of substance.

For the purposes of the present invention, pharmaceutical active ingredients that are sparingly soluble in water are to be understood as meaning those active ingredients which are used for producing drugs for humans and animals, for cosmetic preparations or as food supplements such as vitamins or provitamins or dietetic active ingredients.

Also suitable as sparingly soluble active ingredients to be solubilized are dyes for use in compositions for human or animal nutrition.

Likewise under consideration according to the invention are agrochemical active ingredients for treatment against harmful organisms, such as, for example, insecticides, herbicides or fungicides, and plant growth substances or agents for seed treatment.

Through the present invention are provided, in particular, amphiphilic compounds for use as solubility promoters for pharmaceutical and cosmetic preparations and also for food preparations. They have the property of solubilizing sparingly soluble active ingredients in the field of pharmacy and cosmetics, sparingly soluble food supplements, for example vitamins and carotenoids, but also sparingly soluble active ingredients for use in crop protection compositions (also called pesticides or agrochemical active ingredients), and also veterinary medicine active ingredients.

Further provided by the present invention are, in particular, amphiphilic compounds for use as crystallization inhibitor for pharmaceutical, cosmetic or agrochemical preparations, and for food preparations. Preferably, amphiphilic compounds for use as crystallization inhibitor for agrochemical preparations are provided. They have the property of inhibiting the crystallization of sparingly soluble active ingredients in the field of pharmacy and cosmetics, sparingly soluble food supplements, for example vitamins and carotenoids, but also sparingly soluble active ingredients for use in crop protection compositions (also called pesticides or agrochemical active ingredients), and also veterinary medicine active ingredients Solubilizers for Cosmetics:

According to the invention, the copolymers can be used as solubilizers in cosmetic formulations. For example, they are suitable as solubilizers for cosmetic oils. They have good solubilization ability for fats and oils, such as peanut oil, jojoba oil, coconut oil, almond oil, olive oil, palm oil, *ricinus* oil, soy oil or wheatgerm oil, or for essential oils, such as dwarf-pine oil, lavender oil, rosemary oil, fir needle oil, pine needle oil, eucalyptus oil, peppermint oil, sage oil, bergamot oil, turpentine oil, Melissa oil, juniper oil, lemon oil, anise oil, cardamom oil, peppermint oil, camphor oil, etc. or for mixtures of these oils.

Furthermore, the polymers according to the invention can be used as solubilizers for UV absorbers that are insoluble or sparingly soluble in water, such as, for example, 2-hydroxy-4-methoxybenzophenone (Uvinul® M 40, BASF), 2,2',4,4'-tetrahydroxy-benzophenone (Uvinul® D 50), 2,2'-dihydroxy-4,4'-dimethoxybenzophenone (Uvinul®D49), 2,4-dihydroxybenzophenone (Uvinul® 400), 2'-ethylhexyl 2-cyano-3,3-diphenylacrylate (Uvinul® N 539), 2,4,6-trianilino-p-(carbo-2'-ethylhexyl-1'-oxy)-1,3,5-triazine (Uvinul® T 150), 3-(4-methoxybenzylidene)camphor (Eusolex® 6300, Merck), 2-ethylhexyl N,N-dimethyl-4-aminobenzoate (Eusolex® 6007), 3,3,5-trimethyl-cyclohexyl salicylate, 4-isopropyldibenzoylmethane (Eusolex® 8020), 2-ethylhexyl p-methoxycinnamate and 2-isoamyl p-methoxycinnamate, and mixtures thereof.

The present invention therefore also provides cosmetic preparations which comprise at least one of the copolymers according to the invention of the composition specified at the start as solubilizers. Preference is given to those preparations which, besides the solubilizer, comprise one or more sparingly soluble cosmetic active ingredients, for example the abovementioned oils or UV absorbers.

These formulations are solubilisates based on water or water/alcohol. The solubilizers according to the invention are used in the ratio from 0.2:1 to 20:1, preferably 1:1 to 15:1, particularly preferably 2:1 to 12:1, relative to the sparingly soluble cosmetic active ingredient.

The content of solubilizer according to the invention in the cosmetic preparation is, depending on the active ingredient, in the range from 1 to 50% by weight, preferably 3 to 40% by weight, particularly preferably 5 to 30% by weight.

In addition, further auxiliaries can be added to this formulation, for example nonionic, cationic or anionic surfactants, such as alkyl polyglycosides, fatty alcohol sulfates, fatty alcohol ether sulfates, alkanesulfonates, fatty alcohol ethoxylates, fatty alcohol phosphates, alkylbetaines, sorbitan esters, POE sorbitan esters, sugar fatty acid esters, fatty acid polyglycerol esters, fatty acid partial glycerides, fatty acid carboxylates, fatty alcohol sulfosuccinates, fatty acid sarcosinates, fatty acid isethionates, fatty acid taurates, citric acid esters, silicone copolymers, fatty acid polyglycol esters, fatty acid amides, fatty acid alkanolamides, quaternary ammonium compounds, alkylphenol oxethylates, fatty amine oxethylates, cosolvents such as ethylene glycol, propylene glycol, glycerol etc.

Other constituents which can be added are natural or synthetic compounds, e.g. lanolin derivatives, cholesterol derivatives, isopropyl myristate, isopropyl palmitate, electrolytes, dyes, preservatives, acids (e.g. lactic acid, citric acid).

These formulations are used, for example, in bath additive preparations such as bath oils, aftershaves, face toners, hair tonics, eau de cologne, eau de toilette, and in sunscreen compositions. A further field of use is the oral care sector, for example in mouthwashes, toothpastes, adhesive creams for dentures and the like.

Description of the Solubilization Method:

In the production of the solubilisates for cosmetic formulations, the copolymers according to the invention can be used as 100% strength substance or preferably as aqueous solution.

Usually, the solubilizer is dissolved in water and intensively mixed with the sparingly soluble cosmetic active ingredient to be used in each case.

However, it is also possible to intensively mix the solubilizer with the sparingly soluble cosmetic active ingredient to be used in each case and then to add demineralized water with continuous stirring.

Solubilizers for Pharmaceutical Applications:

The claimed copolymers are likewise suitable for use as solubilizer in pharmaceutical preparations of all types which are characterized in that they can comprise one or more drugs that are insoluble or sparingly soluble in water, as well as vitamins and/or carotenoids. These are in particular aqueous solutions or solubilisates for oral application.

Thus, the claimed copolymers are suitable for use in oral administration forms, such as tablets, capsules, powders, solutions. Here, they can provide the sparingly soluble drug with increased bioavailability. In particular, solid solutions of active ingredient and solubilizer are used.

In the case of parenteral application, besides solubilizates, it is also possible to use emulsions, for example fatty emulsions. For this purpose too, the claimed copolymers are suitable for processing a sparingly soluble drug.

Pharmaceutical formulations of the type specified above can be obtained by processing the claimed copolymers with pharmaceutical active ingredients by conventional methods and using known and new active ingredients.

The use according to the invention can additionally comprise pharmaceutical auxiliaries and/or diluents. Cosolvents, stabilizers, preservatives in particular are listed as auxiliaries.

The pharmaceutical active ingredients used are substances that are slightly soluble or insoluble in water. According to DAB 9 (German pharmacopoeia), the grading of the solubility of pharmaceutical active ingredients is as follows: slightly soluble (soluble in from 30 to 100 parts of solvent); sparingly soluble (soluble in from 100 to 1000 parts of solvent); virtually insoluble (soluble in more than 10 000 parts of solvent). The active ingredients here may be from any indication field.

Examples which may be specified here are benzodiazepines, antihypertensives, vitamins, cytostatics—in particular taxol, anesthetics, neuroleptics, antidepressants, antiviral agents, such as, for example, anti-HIV agents, antibiotics, antimycotics, antidementia drugs, fungicides, chemotherapeutics, urologics, platelet aggregation inhibitors, sulfonamides, spasmolytics, hormones, immunoglobulins, sera, thyroid therapeutic agents, psychopharmacological agents, agents for treating Parkinson's disease and other antihyperkinetic agents, ophthalmics, neuropathy preparations, calcium metabolism regulators, muscle relaxants, anesthetics, lipid-lowering agents, hepatic therapeutic agents, coronary agents, cardiacs, immunotherapeutics, regulatory peptides and their inhibitors, hypnotics, sedatives, gynecological agents, gout remedies, fibrinolytic agents, enzyme preparations and transport proteins, enzyme inhibitors, emetics, circulation-promoting agents, diuretics, diagnostics, corticoids, cholinegenics, bile duct therapeutics, antiasthmatics, broncholytics, beta receptor blockers, calcium antagonists, ACE inhibitors, arteriosclerotics, antiphlogistics, anticoagulants, antihypotonics, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming agents.

One possible production variant is the dissolution of the solubilizer in the aqueous phase, if appropriate with gentle heating, and the subsequent dissolution of the active ingredient in the aqueous solubilizer solution. The simultaneous dissolution of solubilizer and active ingredient in the aqueous phase is likewise possible.

The copolymers according to the invention can also be used as solubilizers in a manner which, for example, involves dispersing the active ingredient in the solubilizer, if appropriate with heating, and mixing it with water with stirring.

Furthermore, the solubilizers can also be processed in the melt with the active ingredients. In particular, solid solutions can be obtained in this way. Of suitability for this is, inter alia, also the method of melt extrusion. A further way of producing solid solutions is also to prepare solutions of solubilizer and active ingredient in suitable organic solvents and then to remove the solvent by customary methods.

The invention therefore also generally provides pharmaceutical preparations which comprise at least one of the copolymers according to the invention as solubilizer. Preference is given to those preparations which, besides the solubilizer, comprise pharmaceutical active ingredient that is insoluble or sparingly soluble in water, for example from the abovementioned indication fields.

Of the abovementioned pharmaceutical preparations, particular preference is given to those which are orally applicable formulations.

The content of solubilizer according to the invention in the pharmaceutical preparation is, depending on the active ingredient, in the range from 1 to 75% by weight, preferably 5 to 60% by weight, particularly preferably 5 to 50% by weight.

A further particularly preferred embodiment relates to pharmaceutical preparations in which the active ingredients and the solubilizer are present as solid solution. Here, the weight ratio of solubilizer to active ingredient is preferably from 1:1 to 4:1, but can be up to 100:1, in particular up to 15:1. What matters is only that, when used in the finished drug form, firstly an effective amount of active ingredient is comprised in the drug form, and secondly in the case of oral drug forms, the forms do not become too large.

Solubilizers for Food Preparations:

Besides use in cosmetics and pharmacy, the copolymers according to the invention are also suitable as solubilizers in the food sector for sparingly water-soluble or water-insoluble nutrients, auxiliaries or additives, such as, for example, fat-soluble vitamins or carotenoids. Examples which may be mentioned are beverages colored with carotenoids.

Solubilizers for Agrochemical Active Ingredients (Pesticides):

In a preferred embodiment of the present invention, the copolymers can be used as solubilizers in agrochemical preparations.

The present invention therefore also provides agrochemical preparations which comprise at least one of the copolymers according to the invention as solubilizers and at least one sparingly soluble pesticide.

In a further preferred embodiment of the present invention, the copolymers can be used as crystallization inhibitors in agrochemical preparations.

The present invention therefore also provides agrochemical preparations which comprise at least one of the copolymers according to the invention as crystallization inhibitors and at least one sparingly soluble pesticide.

The term "sparingly soluble pesticide" refers here to a pesticide that is sparingly soluble in water. According to the invention, as already mentioned above, the term "sparingly soluble in water" here also comprises virtually insoluble substances and means that for a solution of the pesticide in water at 20° C., at least 30 to 100 g of water is required per g of pesticide, preferably at least 100 g of water per 1 g of pesticide. In the case of virtually insoluble pesticides, at least 10 000 g of water per g of substance are required.

Pesticides and agrochemical active ingredients are known to the person skilled in the art from the literature. The term "pesticide" means here at least one active ingredient selected from the group of insecticides, fungicides, herbicides and/or safeners (see Pesticide Manual, 13th Ed. (2003)).

Examples of sparingly soluble pesticides are insecticides, fungicides, herbicides and/or safeners are listed below:

The following list of sparingly soluble insecticides indicates possible active ingredients, but should not be restricted to these:

A.1. organo(thio)phosphates: azinphos-methyl, chlorpyrifos, chlorpyrifos-methyl, chlorfenvinphos, diazinon, disulfoton, ethion, fenitrothion, fenthion, isoxathion, malathion, methidathion, methyl-parathion, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. carbamates: alanycarb, bendiocarb, benfuracarb, carbaryl, carbofuran, carbosulfan, fenoxycarb, furathiocarb, methiocarb, methomyl, oxamyl, pirimicarb, thiodicarb, triazamate;

A.3. pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin;

A.4. growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, a tetronic acid derivative of formula $I^1$,

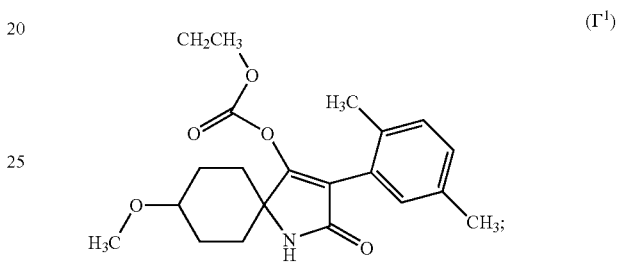

A.5. nicotin receptor agonists/antagonists: clothianidin, dinotefuran, thiacloprid;

A.6. GABA antagonists: acetoprole, endosulfan, ethiprole, fipronil, vaniliprole;

A.7. macrolid insecticides: abamectin, emamectin, milbemectin, lepimectin, spinosad;

A.8. METI I acaricides: fenazaquin, pyridaben, tebufenpyrad, tolfenpyrad;

A.9. METI II and III compound: acequinocyl, fluacyprim, hydramethylnon;

A.10. uncoupler compounds: chlorfenapyr;

A.11. inhibitors of oxidative phosphorylation: cyhexatin, diafenthiuron, fenbutatin oxide, propargite;

A.12. molting disruptor compounds: cryomazine;

A.13. inhibitors of mixed function oxidase: piperonyl butoxide;

A.14. sodium channel blockers: indoxacarb, metaflumizone;

A.15. various: benclothiaz, bifenazate, flonicamid, pyridalyl, pymetrozine, sulfur, thiocyclam and aminoisothiazole compounds of formula $I^2$,

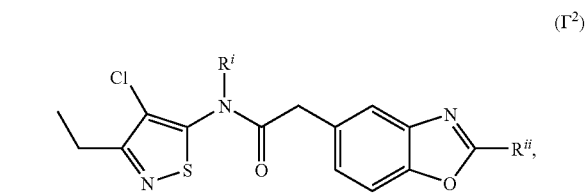

where $R^i$ is —$CH_2OCH_2CH_3$ or H and $R^{ii}$ is $CF_2CF_2CF_3$ or $CH_2CH(CH_3)_3$, anthranilamide compounds of formula $I^3$

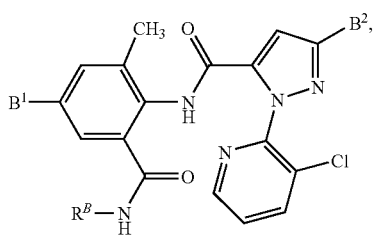

(T³)

where B1 is hydrogen or chlorine, B2 is bromine or CF3, and RB is CH3 or CH(CH3)2, and malononitrile compounds as described in JP 2002 284608, WO 02/89579, WO 02/90320, WO 02/90321, WO 04/06677, WO 04/20399, or JP 2004 99597, N—R'-2,2-dihalo-1-R"cyclopropanecarboxamide-2-(2,6-dichloro-α,α,α,α-tri-fluoro-p-tolyl)hydrazone or N—R'-2,2-di(R''')propionamide-2-(2,6-dichloro-α,α,α,α-trifluoro-p-tolyl)hydrazone, in which R' is methyl or ethyl, halo is chlorine or bromine, R" is hydrogen or methyl and R''' is methyl or ethyl.

The following list of sparingly soluble fungicides indicates possible active ingredients, but should not be limited to these:

1. Strobilurins azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho((2,5-dimethyl-phenyloxymethylene)phenyl)-3-methoxyacrylate;

2. Carboxamides carboxanilides: benalaxyl, benodanil, boscalid, carboxin, mepronil, fenfuram, fenhex-amid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methyl-pyrazole-4-carboxamide, N-(2-cyanophenyl)-3,4-dichloroisothiazole-5-carboxamide; N-(3',4'-dichloro-5-fluorobiphenyl-2-yl)-3-difluoromethyl-1-methylpyrazole-4-carboxamide, N-(2-bicyclopropyl-2-ylphenyl)-3-difluoromethyl-1-methyl-1H-pyrazole-4-carboxamide;

in a further embodiment, examples of carboxanilides are benalaxyl-M, bixafen, isotianil, kiralaxyl, tecloftalam, 2-amino-4-methylthiazole-5-carboxanilide, 2-chloro-N-(1,1,3-tri-methylindan-4-yl)nicotinamide, N-(3',4'-dichloro-5-fluorobiphenyl-2-yl)-3-difluoromethyl-1-methyl-1H-pyrazole-4-carboxamide, N-[2-(1,3-dimethylbutyl)phenyl]-5-fluoro-1,3-dimethyl-1H-pyrazole-4-carboxamide, N-(4'-chloro-3',5-difluorobiphenyl-2-yl)-3-difluoromethyl-1-methyl-1H-pyrazole-4-carboxamide, N-(4'-chloro-3',5-difluorobiphenyl-2-yl)-3-trifluoromethyl-1-methyl-1H-pyrazole-4-carboxamide, N-(3',4'-dichloro-5-fluorobiphenyl-2-yl)-3-trifluoromethyl-1-methyl-1H-pyrazole-4-carboxamide, N-(3',5-difluoro-4'-methylbiphenyl-2-yl)-3-difluoromethyl-1-methyl-1H-pyrazole-4-carboxamide, N-(3',5-difluoro-4'-methylbiphenyl-2-yl)-3-trifluoromethyl-1-methyl-1H-pyrazole-4-carboxamide, N-(2-bicyclopropyl-2-yl-phenyl)-3-difluoromethyl-1-methyl-1H-pyrazole-4-carboxamide, N-(cis-2-bicyclopropyl-2-ylphenyl)-3-difluoromethyl-1-methyl-1H-pyrazole-4-carboxamide, N-(trans-2-bicyclopropyl-2-ylphenyl)-3-difluoromethyl-1-methyl-1H-pyrazole-4-carboxamide;

carboxylic acid morpholides: dimethomorph, flumorph;

benzoamides: flumetover, fluopicolide (picobenzamid), zoxamide; in a further embodiment, one example of benzoamide is N-(3-ethyl-3,5,5-trimethylcyclohexyl)-3-formylamino-2-hydroxybenzamide;

other carboxamides: carpropamid, diclocymet, mandipropamid, N-(2-(4-[3-(4-chloro-phenyl)prop-2-ynyloxy]-3-methoxyphenyl)ethyl)-2-methanesulfonylamino-3-methyl-butyramide, N-(2-(4-[3-(4-chlorophenyl)prop-2-ynyloxy]-3-methoxyphenyl)ethyl)-2-ethanesulfonylamino-3-methylbutyramide, N-(3',4'-dichloro-5-fluorobiphenyl-2-yl)-3-difluoromethyl-1-methyl-1H-pyrazole-4-carboxamide and N-(2-bicyclopropyl-2-yl-phenyl)-3-difluoromethyl-1-methyl-1H-pyrazole-4-carboxamide; in a further embodiment examples of other carboxamides are oxytetracyclin, silthiofam, N-(6-methoxypyridin-3-yl) cyclopropanecarboxamide.

3. Azoles triazoles: bitertanol, bromuconazole, cyproconazole, difenoconazole, diniconazole, enilconazole, epoxiconazole, fenbuconazole, flusilazole, fluquinconazole, flutriafol, hexaconazol, imibenconazole, ipconazole, metconazole, myclobutanil, penconazole, propiconazole, prothioconazole, simeconazole, tebuconazole, tetraconazole, triadimenol, triadimefon, triticonazole;

imidazoles: cyazofamid, imazalil, pefurazoate, prochloraz, triflumizole;

benzimidazoles: benomyl, carbendazim, fuberidazole, thiabendazole;

others: ethaboxam, etridiazole, hymexazole;

4. Nitrogen-Containing Heterocyclyl Compounds:

pyridines: fluazinam, pyrifenox, 3-[5-(4-chlorophenyl)-2,3-dimethylisoxazolidin-3-yl]pyridine;

pyrimidines: bupirimate, cyprodinil, ferimzone, fenarimol, mepanipyrim, nuarimol, pyrimethanil;

piperazines: triforine;

pyrroles: fludioxonil, fenpiclonil;

morpholines: aldimorph, dodemorph, fenpropimorph, tridemorph;

dicarboximides: iprodione, procymidone, vinclozolin;

others: acibenzolar-S-methyl, anilazin, captan, captafol, dazomet, diclomezine, fenoxanil, folpet, fenpropidin, famoxadone, fenamidone, octhilinone, probenazole, proquinazid, quinoxyfen, tricyclazole, 5-chloro-7-(4-methylpiperidin-1-yl)-6-(2,4,6-trifluorophenyl)[1,2,4]triazolo[1,5-a]pyrimidine, 2-butoxy-6-iodo-3-propyl-chromen-4-one, N-dimethyl-3-(3-bromo-6-fluoro-2-methylindole-1-sulfonyl)[1,2,4]triazole-1-sulfonamide;

5. Carbamates and Dithiocarbamates carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl) ethanesulfonyl)but-2-yl)carbamate;

6. Other Fungicides organometallic compounds: fentin salts;

sulfur-containing heterocyclyl compounds: isoprothiolane, dithianon;

organophosphorus compounds: edifenphos, fosetyl, fosetyl-aluminum, iprobenfos, pyrazophos, tolclofos-methyl, phosphorous acid and its salts;

organochlorine compounds: thiophanate methyl, chlorothalonil, dichlofluanid, tolylfluanid, flusulfamide, phthalide, hexachlorbenzene, pencycuron, quintozene;

nitrophenyl derivatives: binapacryl, dinocap, dinobuton;

others: spiroxamine, cyflufenamid, cymoxanil, metrafenone.

The following list of sparingly soluble herbicides indicates possible active ingredients, but should not be limited to these:

Compounds which inhibit the biosynthesis of lipids, for example chlorazifop, clodinafop, clofop, cyhalofop, ciclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, and their esters, butroxydim, cycloxydim, profoxydim, sethoxydim, tepraloxydim, tralkoxydim, butylate, cycloat, diallat, dimepiperat, EPTC, esprocarb, ethiolate, isopolinate, methiobencarb, molinate, orbencarb, pebulate, prosulfocarb, sulfallat, thiobencarb, thiocarbazil, triallat, vernolat, benfuresat, ethofumesat und bensulid;

ALS inhibitors, such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac; if the pH is <8;

Compounds which inhibit the photosynthesis, such as atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine and terbutryne;

Protoporphyrinogen-IX oxidase inhibitors, such as acifluorfen, bifenox, cchlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

Herbicides such as metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethyl-phenyl)pyrimidine, and 3-heterocyclyl-substituted benzoyl derivatives of the formula (cf. WO-A-96/26202, WO-A-97/41116, WO-A-97/41117 and WO-A-97/41118)

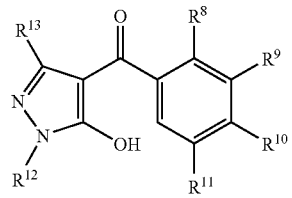

in which the substituents $R^8$ to $R^{13}$ have the following meanings:

$R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-halo-alkoxy, $C_1$-$C_6$-alkylthio, $C_1$-$C_6$-alkylsulfinyl or $C_1$-$C_6$-alkylsulfonyl;

$R^9$ is a heterocyclic radical from the group consisting of thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, in which the specified radicals can carry one or more substituents, for example may be mono-, di-, tri- or tetra-substituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$=hydrogen, halogen or $C_1$-$C_6$-alkyl;

$R^{12}$=$C_1$-$C_6$-alkyl;

$R^{13}$=hydrogen or $C_1$-$C_6$-alkyl.

If the pH is <8.

Mitosis inhibitors such as benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, chlorthal, carbetamide, chlorpropham and propham;

VLCFA inhibitors such as acetochlor, alachlor, butachlor, butenachlor, delachlor, diethatyl, dimethachlor, dimethenamid, dimethenamid-p, metazachlor, metolachlor, S-metolachlor, pretilachlor, propisochlor, prynachlor, terbuchlor, thenylchlor, xylachlor, CDEA, epronaz, diphenamid, napropamide, naproanilide, pethoxamid, flufenacet, mefenacet, fentrazamide, anilofos, piperophos, cafenstrole, indanofan and tridiphan;

Inhibitors for the biosynthesis of cellulose, such as dichlobenil, chlorthiamid, isoxaben and flupoxam;

Herbicides such as dinofenat, dinoprop, dinosam, dinoseb, dinoterb, DNOC, etinofen and medinoterb;

Furthermore: benzoylprop, flamprop, flamprop-M, bromobutide, chlorflurenol, cinmethylin, methyldymron, etobenzanid, pyributicarb, oxaziclomefone, triaziflam and methyl bromide.

The following list indicates possible sparingly soluble safeners, but should not be restricted to these:

benoxacor, cloquintocet, cyometrinil, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine (R-29148), 4-(dichloro-acetyl)-1-oxa-4-azaspiro[4.5]decane (AD-67; MON 4660) and oxabetrinil.

Preferred fungicides are triazoles such as bitertanol, bromuconazole, cyproconazole, difenoconazole, diniconazole, enilconazole, epoxyconazole, fenbuconazole, flusilazole, fluquinconazole, flutriafol, hexaconazol, imibenconazole, ipconazole, metconazole, myclobutanil, penconazole, propiconazole, prothioconazole, simeconazole, tebuconazole, tetraconazole, triadimenol, triadimefon, triticonazole, strobilurine such as azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho ((2,5-dimethylphenyloxymethylene)phenyl)-3-methoxyacrylate, and 5-chloro-7-(4-methyl-piperidin-1-yl)-6-(2,4,6-trifluorophenyl)[1,2,4]triazolo[1,5-a]pyrimidine and boscalid.

Very particularly preferred fungicides are epoxyconazole, metconazole, pyraclostrobin, kresoxim-methyl and 5-chloro-7-(4-methylpiperidin-1-yl)-6-(2,4,6-trifluoro-phenyl)[1,2,4]triazolo[1,5-a]pyrimidine and boscalid.

Preferred insecticides are metaflumizon, fipronil and alpha-cypermethrin.

In a further preferred embodiment, mixtures comprising at least two different triazoles are preferred, in particular mixtures comprising metconazole and epoxyconazole, metconazole and prothioconazole, or epoxyconazole and prothioconazole.

In a further preferred embodiment, mixtures comprising at least one triazole and at least one strobilurin are preferred. Specifically, mixtures comprising pyraclostrobin and epoxyconazole, and mixtures comprising pyraclostrobin and metconazole are preferred.

In a further preferred embodiment, mixtures comprising at least one triazole and at least one carboxamide are preferred. In particular, preference is given to mixtures which comprise at least one triazole, at least one carboxamide and at least one strobilurin.

In the agrochemical preparations, the mass ratio of polymer:active ingredient is 1:10 (w/w) to 100:1 (w/w), preferably 1:2 (w/w) to 50:1 (w/w), particularly preferably 1:1 (w/w) to 10:1 (w/w), particularly preferably 2:1 (w/w) to 10:1 (w/w).

The agrochemical preparations can furthermore also comprise auxiliaries customary for the formulation of pesticides, the choice of auxiliaries being governed by the particular application form and the active ingredient.

As a rule, the amount of auxiliaries used is between 0 and 60% by weight, preferably 0.1 and 30% by weight.

Examples of auxiliaries suitable for the formulation of pesticides are solvents, solid carriers, surface-active substances (such as further solubilizers, protective colloids, wetting agents and adhesives), organic and inorganic thickeners, bactericides, antifreezes, antifoams.

Examples of thickeners (i.e. compounds which impart a modified flow behavior to the formulation, i.e. high viscosity in the resting state and low viscosity in the moving state) are polysaccharides, and also organic and inorganic layered minerals such as xanthan gum (Kelzan® from Kelco), Rhodopol® 23 (Rhone Poulenc) or Veegum® (R.T. Vanderbilt) or Attaclay® (Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Examples of bactericides are bactericides based on dichlorophen and benzyl alcohol hemiformal (Proxel® from ICI or Acticide® RS from Thor Chemie and Kathon® MK from Rohm & Haas), and isothiazolinone derivatives, such as alkylisothiazolinones and benzisothiazolinones (Acticide MBS from Thor Chemie).

Examples of antifreezes are ethylene glycol, propylene glycol, urea or glycerol.

Suitable solvents are organic solvents such as mineral oil fractions of medium to high boiling point, such as kerosene and diesel oil, also coal tar oils, and oils of vegetable or animal origin, aliphatic, cyclic and aromatic hydrocarbons, e.g. paraffins, tetrahydronaphthalene, alkylated naphthalenes and derivatives thereof, alkylated benzenes and derivatives thereof, alcohols, such as methanol, ethanol, propanol, butanol and cyclohexanol, ketones, such as cyclohexanone, strongly polar solvents, for example amines such as N-methylpyrrolidone, and mixtures of the above-mentioned solvents and water, and also mixtures of water and organic solvents.

Solid carriers are mineral earths such as silicas, silica gels, silicates, talc, kaolin, limestone, lime, chalk, bolus, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and vegetable products such as cornmeal, bark dust, sawdust, nutshell meal, cellulose powder or other solid carriers.

Suitable surface-active substances (adjuvants, wetting agents, adhesives, dispersants or emulsifiers) are the alkali metal salts, alkaline earth metal salts, ammonium salts of aromatic sulfonic acids, e.g. lignin (Borresperse grades Borregaard), phenol, naphthalene (Morwet grades, Akzo Nobel) and dibutylnaphthalenesulfonic acid (Nekal grades BASF), and of fatty acids, alkyl- and alkylarylsulfonates, alkyl sulfates, lauryl ether sulfates and fatty alcohol sulfates, and salts of sulfated hexa-, hepta- and octadecanols, and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octyl phenol ether, ethoxylated isooctyl-, octyl- or nonylphenol, alkylphenyl, tributylphenyl polyglycol ethers, alkylaryl polyether alcohols, isotridecyl alcohol, fatty alcohol ethylene oxide condensates, ethoxylated *ricinus* oil, polyoxyethylene or polyoxypropylene alkyl ethers, lauryl alcohol polyglycol ether acetate, sorbitol esters, lignin sulfite spent liquors, and proteins, denatured proteins, polysaccharides (e.g. methylcellulose), hydrophobically modified starches, polyvinyl alcohol (Mowiol grades Clariant), polycarboxylate (BASF Sokalan grades), polyalkoxylates, polyvinylamine (BASF Lupamin grades), polyethyleneimine (BASF Lupasol grades), polyvinylpyrrolidone and copolymers thereof.

Examples of various types of agrochemical preparations in which the copolymers according to the invention can be used are pastes, pastilles, wettable powders, dusts (WP, SP, SS, WS, DP, DS) or granules (WG, GR, FG, GG, MG) or tablet preparations (TB, WT), which may either be soluble or dispersible (wettable) in water.

The agrochemical preparations (e.g. OD, FS, WG, SG, WP, SP, SS, WS)) are generally used in diluted form. Formulation types such as DP, DS, GR, FG, GG, MG are usually used neat.

Preference is given to the above defined types of agrochemical preparations WG, WP, GR, WT and TB.

The production of agrochemical formulations and the technology required for this is known to the person skilled in the art (see U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pp. 8-57 and ff. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095, 558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Federal Republic of Germany), 2001).

All of the embodiments of the abovementioned agrochemical preparations are referred to below as "agrochemical preparations according to the invention".

The present invention also claims methods of controlling undesired plant growth wherein the undesired plants, the ground on which the undesired plants grow, or their seeds are treated with an agrochemical preparation according to the invention.

Furthermore, the present invention claims methods of controlling undesired insect or mite attack on plants and/or for controlling phytopathogenic fungi, wherein the fungi/insects, their habitat or the plants or ground to be protected against fungal or insect attack and the plants, the ground on which the plants grow, or seeds thereof are treated with an agrochemical preparation according to the invention.

The term phytopathogenic fungi describes, but is not restricted to, the following species: *Alternaria* spp. on rice, vegetables, soybeans, rapeseed, sugar beet and fruits, *Aphanomyces* spp. on sugar beet and vegetables, *Bipolaris* and *Drechslera* spp. corn, cereals, rice and cultivated lawns, *Blumeria graminis* (powdery mildew) on cereals, *Botrytis cinerea* (gray mold) on strawberries, vegetables, cultivated flowers, grapes, *Bremia lactucae* on lettuce, *Cercospora* spp. on corn, soybeans and sugar beet, *Cochliobolus* spp. on corn, cereals, rice (e.g. *Cochliobolus sativus* on cereals, *Cochliobolus miyabeanus* on corn), *Colletotrichum* spp. on soybeans and cotton, *Drechlsera* spp. on cereals and corn, *Exserohlilum* spp. on corn, *Erysiphe cichoracearum* and *Sphaerotheca fuliginea* on cucumbers, *Erysiphe necator* on grapes, *Fusarium* and *Verticillium* spp. on various plants, *Gaeumannomyces graminis* on cereals, *Gibberella* spp. on cereals and rice (e.g. *Gibberella fujikuroi* on rice, *Gibberella zeae* on cereals), grainstaining complex on rice, *Microdochium nivale* on cereals, *Mycosphaerella* spp. on cereals, bananas and peanuts, *Phakopsora pachyrhizi* and *Phakopsora meibomiae* on soybeans, *Phomopsis* spp. on soybeans and sunflowers, *Phytophthora infestans* on potatoes and tomatoes, *Plasmopara viticola* on grapes, *Podosphaera leucotricha* on apples, *Pseudocercosporella herpotrichoides* on wheat and barley, *Pseudoperonospora* spp. on hops and cucumbers, *Puccinia* spp. on cereals and corn, *Pyrenophora* spp. on cereals, *Pyricularia oryzae* on rice, *Cochliobolus miyabeanus* and *Corticium sasakii* (*Rhizoctonia solani*), *Fusarium semitectum* (and/or *moniliforme*), *Cercospora oryzae*, *Sarocladium oryzae*, *S attenuatum*, *Entyloma oryzae*, *Gibberella fujikuroi* (bakanae), Grainstaining complex (various pathogens), *Bipolaris* spp., *Drechslera* spp. and *Pythium* and *Rhizoctonia* spp. on rice, corn, cotton, sunflowers, rapeseed (canola, oilseed rape), vegetables, lawns, nuts and other plants, *Rhizoctonia solani* on potatoes, *Sclerotinia* spp. on types of rapeseed (canola/oilseed rape) and sunflowers, *Septoria tritici* and *Stagonospora nodorum* on wheat, *Uncinula necator* on grapes, *Sphacelotheca reiliana* on corn, *Thievaliopsis* spp. on soybeans and cotton, *Tilletia* spp. on cereals, *Ustilago* spp. on cereals, corn, sugar beet and *Venturia* spp. (scab) on apples and pears;

The term undesired insects or mites describes, but is not restricted to, the following genera:

Millipedes (Diplopoda), for example *Blaniulus* spp

Ants (Hymenoptera), for example *Atta capiguara*, *Atta cephalotes*, *Atta laevigata*, *Atta robusta*, *Atta sexdens*, *Atta texana*, *Monomorium pharaonis*, *Solenopsis geminata*, *Solenopsis invicta*, *Pogonomyrmex* spp and *Pheidole megacephala*, Beetles (Coleoptera), for example *Agrilus sinuatus*, *Agriotes lineatus*, *Agriotes obscurus* and other *Agriotes* spp, *Amphimallus solstitialis*, *Anisandrus dispar*, *Anthonomus grandis*, *Anthonomus pomorum*, *Aracanthus morei*, *Atomaria linearis*, *Blapstinus* spp, *Blastophagus piniperda*, *Blitophaga undata*, *Bothynoderes punciventris*, *Bruchus ruflmanus*, *Bruchus pisorum*, *Bruchus lentis*, *Byctiscus betulae*, *Cassida nebulosa*, *Cerotoma trifurcata*, *Ceuthorrhynchus assimilis*, *Ceuthorrhynchus napi*, *Chaetocnema tibialis*, *Conoderus vesperitmus* and other *Conoderus* spp, *Conorhynchus mendicus*, *Crioceris asparagi*, *Cylindrocopturus adspersus*, *Diabrotica* (*longicornis*) *barberi*, *Diabrotica* semi-punctata, *Diabrotica speciosa*, *Diabrotica undecimpunctata*, *Diabrotica virgifera* and other *Diabrotica* spp, *Eleodes* spp, *Epilachna varivestis*, *Epitrix hirtipennis*, *Eutinobothrus brasiliensis*, *Hylobius abietis*, *Hypera brunneipennis*, *Hypera postica*, *Ips typographus*, *Lema bilineata*, *Lema melanopus*, *Leptinotarsa decemlineata*, *Limonius californicus* and other *Limonius* spp, *Lissorhoptrus oryzophilus*, *Listronotus bonariensis*, *Melanotus communis* and other *Melanotus* spp, *Meligethes aeneus*, *Melolontha hippocastani*, *Melolontha melolontha*, *Oulema oryzae*, *Ortiorrhynchus sulcatus*, *Oryzophagus oryzae*, *Otiorrhynchus ovatus*, *Oulema oryzae*, *Phaedon cochleariae*, *Phyllotreta chrysocephala*, *Phyllophaga cuyabana* and other *Phyllophaga* spp, *Phyllopertha horticola*, *Phyllotreta nemorum*, *Phyllotreta striolata*, and other *Phyllotreta* spp, *Popillia japonica*, *Promecops carinicollis*, *Premnotrypes voraz*, *Psylliodes* spp, *Sitona lineatus*, *Sitophilus granaria*, *Sternechus pinguis*, *Sternechus subsignatus*, and *Tanymechus palliatus* and other *Tanymechus* spp, Flies (Diptera), for example *Agromyza oryzea*, *Chrysomya bezziana*, *Chrysomya hominivorax*, *Chrysomya macellaria*, *Contarinia sorghicola*, *Cordylobia anthropophaga*, *Dacus cucurbitae*, *Dacus oleae*, *Dasineura brassicae*, *Delia antique*, *Della coarctata*, *Delia platura*, *Delia radicum*, *Fannia canicularis*, *Gasterophilus intestinalis*, *Geomyza Tripunctata*, *Glossina morsitans*, *Haematobia irritans*, *Haplodiplosis equestris*, *Hypoderma lineata*, *Liriomyza sativae*, *Liriomyza trifolii*, *Lucilia caprina*, *Lucilia cuprina*, *Lucilia sericata*, *Lycoria pectoralis*, *Mayetiola destructor*, *Muscina stabulans*, *Oestrus ovis*, *Opomyza florum*, *Oscinella frit*, *Pegomya hysocyami*, *Phorbia antiqua*, *Phorbia brassicae*, *Phorbia coarctata*, *Progonya leyoscianil*, *Psila rosae*, *Rhagoletis cerasi*, *Rhagoletis pomonella*, *Tabanus bovinus*, *Tetanops myopaeformis*, *Tipula oleracea* and *Tipula paludosa*, Heteroptera (Heteroptera), for example *Acrosternum hilare*, *Blissus leucopterus*, Cicadellidae for example *Empoasca fabae*, Chrysomelidae, *Cyrtopeltis notatus*, Delpahcidae, *Dysdercus cingulatus*, *Dysdercus intermedius*, *Eurygaster integriceps*, *Euschistus impictiventris*, *Leptoglossus phyllopus*, *Lygus lineolaris*, *Lygus pratensis*, *Nephotettix* spp, *Nezara viridula*, Pentatomidae, *Piesma quadrata*, *Solubea insularis* and *Thyanta perditor*, Aphids and other homoptera, for example *Acyrthosiphon onobrychis*, *Adelges laricis*, *Aphidula nasturtii*, *Aphis fabae*, *Aphis forbesi*, *Aphis glycines*, *Aphis gossypii*, *Aphis grossulariae*, *Aphis pomi*, *Aphis schneideri*, *Aphis spiraecola*, *Aphis sambuci*, *Acyrthosiphon pisum*, *Aulacorthum solani*, *Brachycaudus cardui*, *Brachycaudus helichrysi*, *Brachycaudus persicae*, *Brachycaudus prunicola*, *Brevicoryne brassicae*, *Capitophorus horni*, *Cerosipha gossypii*, *Chaetosiphon fragaefolii*, *Cryptomyzus ribis*, *Dreyfusia nordmannianae*, *Dreyfusia piceae*, *Dysaphis radicola*, *Dysaulacorthum pseudosolani*, *Dysaphis plantaginea*, *Dysaphis pyri*, *Empoasca fabae*, *Hyalopterus pruni*, *Hyperomyzus lactucae*, *Macrosiphum avenae*, *Macrosiphum euphorbiae*, *Macrosiphon rosae*, *Megoura viciae*, *Melanaphis pyrarius*, *Metopolophium dirhodum*, *Myzodes* (*Myzus*) *persicae*, *Myzus ascalonicus*, *Myzus cerasi*, *Myzus varians*, *Nasonovia ribis-nigri*, *Nilaparvata lugens*, *Pemphigus bursarius*, *Pemphigus populivenae*, and other *Pemphigus* spp, *Perkinsiella saccharicida*, *Phorodon humuli*, Psyllidae, for example *Psylla mali*, *Psylla piri* and other *Psylla* spp, *Rhopalomyzus ascalonicus*, *Rhopalosiphum maidis*, *Rhopalosiphum padi*, *Rhopalosiphum insertum*, *Sappaphis mala*, *Sappaphis mali*, *Schizaphis graminum*, *Schizoneura lanuginosa*, *Sitobion avenae*, *Trialeurodes vaporariorum*, *Toxoptera aurantii*and, und *Viteus vitifolii*, Lepidoptera, for example *Agrotis ypsilon*, *Agrotis segetum* and other *Agrotis* spp, *Alabama argilacea*, *Anticarsia gemmatalis*, *Argyresthia conjugella*, *Autographa gamma*, *Bupalus piniarius*, *Cacoecia murinana*, *Capua reticulana*,

*Cheimatobia brumata, Chilo suppresalis* and other *Chilo* spp, *Choristoneura fumiferana, Choristoneura occidentalis, Cirphis unipuncta, Cnaphlocrocis medinails, Cydia pomonella, Dendrolimus pini, Diaphania nitidalis, Diatraea grandiosella, Earias insulana, Elasmopalpus lignosellus, Eupoeclia ambiguella, Euxoa* spp, *Evetria bouliana, Feltia subterranea, Galleria mellonella, Grapholitha funebrana, Grapholitha molesta, Heliothis armigera, Heliothis virescens, Heliothis zea, Hellula undais, Hibernia defoliaria, Hyphantria cunea, Hyponomeuta malinellus, Keiferia lycopersicella, Lambdina fiscellaria, Laphygma exigua, Lerodea eufala, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Momphidae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sesamia nonagrioides* and other *Sesamia* spp, *Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, Orthoptera, for example, Acrididae, *Acheta domestica, Blatta orientalis, Blattella germanica, Forficula auricularia, Gryllotalpa gryllotalpa, Locusta migratoria, Melanoplus biviltatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Termites (Isoptera), for example *Calotermes flavicollis, Coptotermes* spp, *Dalbulus maidis, Leucotermes flavipes, Macrotermes gilvus, Reticulitermes lucifugus* and Termes natalensis;

*Thrips* (Thysanoptera) for example *Frankliniella fusca, Frankliniella occidentalis, Frankliniella tritici* and other *Frankliniella* spp, *Scirtothrips citri, Thrips oryzae, Thrips palmi, Thrips simplex* and *Thrips tabaci,*

Arachnoidea, for example arachnids (Acarina), for example of the families Argasidae, Ixodidae and Sarcoptidae, for example *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei*, und Eriophyidae spp e.g. *Aculus schlechtendali, Phyllocoptrata oleivora* und *Eriophyes sheldoni;* Tarsonemidae spp e.g. *Phytonemus pallidus* und *Polyphagotarsonemus latus;* Tenuipalpidae spp e.g. *Brevipalpus phoenicis,* Tetranychidae spp e.g. *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;*

Nematodes, in particular plant parasitic nematodes, for example "root knot" nematodes, *Meloidogyne hapla, Meloidogyne incognita, Meloidogyne javanica,* and other *Meloidogyne* spp; cyst-forming nematodes, *Globodera rostochiensis* and other *Globodera* spp; *Heterodera avenae, Heterodera glycines, Heterodera schachili, Heterodera trifolii,* and other *Heterodera* spp; seed gall nematodes, *Anguina* spp; stem and foliar nematodes, *Aphelenchoides* spp; sting nematodes, *Belonolaimus longicaudatus* and other *Belonolaimus* spp; pine nematodes, *Bursaphelenchus xylophilus* and other *Bursaphelenchus* spp; ring nematodes, *Criconema* spp, *Criconemella* spp, *Criconemoides* spp, *Mesocriconema* spp; stem and bulb nematodes, *Ditylenchus destructor, Ditylenchus dipsaci* and other *Ditylenchus* spp; Awl nematodes, *Dolichodorus* spp; spiral nematodes, *Heliocotylenchus mutlicinctus* and other *Helicotylenchus* spp; sheath and sheathoid nematodes, *Hemicycliophora* spp and *Hemicriconemoides* spp; *Hirshmanniella* spp; lance nematodes, *Hoploaimus* spp; false rootknot nematodes, *Nacobbus* spp; needle nematodes, *Longidorus elongatus* and other *Longidorus* spp; lesion nematodes, *Pratylenchus neglectus, Pratylenchus penetrans, Pratylenchus curvilatus, Pratylenchus goodeyl* and other *Pratylenchus* spp; Burrowing nematodes, *Radopholus similis* und andere *Radopholus* spp; Reniform nematodes, *Rotylenchus robustus* and other *Rotylenchus* spp; *Scutellonema* spp; Stubby root nematodes, *Trichodorus primitivus* and other *Trichodorus* spp, *Paratrichodorus* spp; Stunt nematodes, *Tylenchorhynchus claytoni, Tylenchorhynchus dubius* and other *Tylenchorhynchus* spp; Citrus nematodes, *Tylenchulus* spp; Dagger nematodes, *Xiphinema* spp; and other plant parasitic nematodes.

Control of undesired plant growth means the control/destruction of plants which grow in places where they are undesired, for example Dicotyledonous plants of the species: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum*. Monocotyledonous plants of the species: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera*

The copolymers according to the invention are characterized by a particularly good solubilizing effect. They are also able to form so-called solid solutions with sparingly soluble substances. According to the invention, solid solutions is the term used to refer to systems in which, upon visual inspection, no crystalline fractions of the sparingly soluble substance are to be seen. Furthermore, upon visual inspection of the stable solid solutions, no amorphous constituents are to be seen either. Visual inspection takes place using a light microscope at 40 times magnification.

Furthermore, the copolymers according to the invention are characterized in that they increase the bioavailability of active ingredients. In addition, it is advantageous that the copolymers according to the invention in agrochemical preparations have extremely low phytotoxicity. Furthermore, the copolymers according to the invention are characterized by a particularly good crystallization-inhibiting effect for active ingredients that are sparingly soluble in water.

Hitherto, attempts have been made to solve the problems of solubilization and crystal inhibition using various compounds. However, a compound which can solve both problems is desirable. A particular advantage of the copolymers according to the invention is that preparations of active ingredients that are sparingly soluble in water can now make do with just one additive which acts both as solubilizer and as crystallization inhibitor.

In the examples below, the preparation and use of the copolymers according to the invention is explained in more detail.

EXAMPLES

Abbreviations

VP (N-vinylpyrrolidone)
VAc (vinyl acetate)
PVP (polyvinylpyrrolidone)
PVAc (polyvinyl acetate)
AIBN (azobisisobutyronitrile)
PVP-b-PVAc (block copolymer of PVP and PVAc)
DMF (dimethylformamide)

A) Preparation of the Block Copolymers

General Procedure

Firstly, 200 g of N-vinylpyrrolidone, 1.76 g of 2-(ethoxycarbonothioyl)thiopropionic acid and 0.15 g of AIBN in 200 g of dioxane were mixed and this mixture was heated to 70° C. The mixture was held at this temperature for 8 h, then cooled to room temperature and the resulting polymer was precipitated out by adding 100 ml of diethyl ether.

The resulting polymer was then mixed with 50 g of vinyl acetate and 0.05 g of AIBN in 75 g of dioxane and the mixture is heated to 70° C. After 8 h, the solvent was removed in vacuo and the polymer was dried at 70° C. in a vacuum drying cabinet.

| Ex. No | PVP-PVAc [mol %] use amounts | PDI* | $M_n$ | Solubility in water |
|---|---|---|---|---|
| 1 | 90-10 | 1.6 | 14800 | soluble |
| 2 | 80-20 | 1.8 | 13200 | soluble |
| 3 | 70-30 | 2 | 12900 | soluble |
| 4 | 60-40 | 1.9 | 13900 | soluble |
| 5 | 50-50 | 2 | 17600 | soluble |
| 5 | 40-60 | 2.3 | 19200 | micellarly dispersible |
| 6 | 30-70 | 2.2 | 16300 | micellarly dispersible |
| 7 | 20-80 | 2.5 | 16900 | micellarly dispersible |
| 8 | 10-90 | 2.4 | 17800 | micellarly dispersible |

*Polydispersity index determined by means of gel permeation chromatography calculated as PDI = $M_w$:$M_n$.

B) Solubilization of Dyes from Solid Solution

B1)

A dye (Dianix Luminous Red, Dystar) and the polymer as in Ex. 4 were mixed in the weight ratio dye:polymer 33:67 and dissolved in DMF, and the solvent was then removed in a drying cabinet. The solid solution obtained in this way was taken up with sufficient water to give a 3% strength by weight solution, based on the polymer content, and filtered over a 0.45 µm Millipore filter, and the dye content was determined by means of HPLC/UV. Result: 10 mg/kg of dye dissolved in water.

For comparison, the polymer used was copovidone, a random copolymer of 60% by weight of VP and 40% by weight of VAc. Result: 2 mg/kg dye dissolved in water. The comparison shows that, in the presence of the block copolymer, five times more dye is solubilized than in the presence of a comparable random copolymer not in accordance with the invention.

B2)

Furthermore, solid solutions as described above were prepared with the dye, block copolymer and, for comparison, with PVP homopolymers (PVP K90, K30, K17) and VP-VAc copolymer 60/40 (copovidone) and dissolved in water, and the solutions were assessed visually for color intensity. The greater the color intensity, the greater the solubilization. The table shows that the PVP homopolymers not according to the invention and the random copolymer dissolve the dye less well than comparable block copolymers according to the invention.

| PVP K90 | PVP K30 | PVP K17 | Copovidone | PVP-b-PVAc 80-20 | PVP-b-PVAc 50-50 |
|---|---|---|---|---|---|
| pale yellow | pale pink | pale pink | pink | bright red | intense red |

C) Solubilization of Active Ingredient from Solid Solution

Furthermore, the solubilization in water of pharmaceutical active ingredients from the solid solution was investigated at 37° C. (*50-50 based on use amounts). The comparison shows that, in the presence of the block copolymer, six times more active ingredient is solubilized than in the presence of a comparable random copolymer copovidone not according to the invention.

|  | Solubilization of estradiol [mg/kg] | Solubilization of clotrimazol [mg/kg] |
|---|---|---|
| PVP-b-PVAc 50-50* | 0.06 | 0.06 |
| Copovidone | 0.01 | 0.01 |

D) Solubilization of Agrochemical Active Ingredients from Solid Solution

Solubility in water of the agrochemical active ingredients used:

Epoxyconazole: $6.63*10^{-4}$ g/100 ml (20° C.).
Metconazole: 30.4 mg/l (20° C.).
Pyraclostrobin: 1.9 mg/l (20° C.).

The fungicidal effect of various formulations of the agrochemical active ingredients epoxyconazole, metconazole and pyraclostrobin as a function of the concentration of applied active ingredient was assessed in comparison with block copolymers and random polymer.

For this, one or more agrochemical active ingredient and the block copolymer as in Ex. 4 was mixed in the weight ratio active ingredient:polymer 1:2 and dissolved in DMF, and the solvent was then removed in a drying cabinet. The solid solution obtained in this way was taken up with sufficient water to give a 15% strength by weight polymer concentration, based on the aqueous solution (corresponds to 30% by weight of active ingredient or active ingredient mixture, based on the aqueous solution). For the application, the aqueous solution was further diluted with water so that a concentration of the aqueous solution of 0, 8, 16, 32, 64 or 100 ppm, based on the applied aqueous formulation, were obtained. The determination of the damage picture was carried out on wheat of the Kanzler variety which had been infected beforehand with the fungal species *Puccinia recondita* (experiments F-0 to F-4).

For comparison, the process was repeated with the comparable VP-VAc copolymer 60/40 (copovidone, random copolymer of 60% by weight VP and 40% by weight of VAc) (comparative experiments C-0 to C-4). The control experiments K-1 to K-3 were carried out without active ingredient.

The column "composition" shows the qualitative and quantitative composition of the particular copolymer with which the active ingredient is present in the aqueous solution.

For all of the formulations, the weight ratio of polymer to active ingredient was 2 to 1. The column "applied concentration" indicates in which concentration the active ingredient formulations was applied. The column "plant appraisal" indicates, on a scale from 0 to 100, the remaining fungal attack following treatment, where 100 means complete attack. The stated value is a mean from three individual values. "n.a" means not applicable.

The control experiments without active ingredient have shown that the block copolymers exhibit low phytotoxicity, which is the same as or lower than in the case of comparable random copolymers.

These comparative experiments show that, at the same active ingredient concentration, with the polyvinyllactam-polyvinyl acetate block copolymers used according to the invention as solubilizers, considerably better agrochemical effects are to be achieved than in the presence of comparable random polyvinyllactam-polyvinyl acetate copolymers. This demonstrates the better bioavailability of the agrochemical active ingredients by using the block copolymers as solubilizers.

| No. | Composition | Applied concentration [ppm] | Plant appraisal |
|---|---|---|---|
| K-1 | Without active ingredient, without polymer | 0 | 85 |
| k-2 | VP-VAc (60:40), without active ingredient | 100 | 80 |
| K-3 | Random VP-VAc (60:40), without active ingredient | 100 | 80 |
| F-0 | VP-VAc (60:40) + epoxyconazole | 16 | 0 |
|  |  | 8 | 0 |
|  |  | 4 | 5 |
| F-1 | VP-VAc (60:40) + metconazole | 32 | 0 |
|  |  | 16 | 4 |
|  |  | 8 | 4 |
| F-2 | VP-VAc (60:40) + metconazole/epoxyconazole (3:2) | 32 | 0 |
|  |  | 16 | 0 |
|  |  | 8 | 4 |
| F-3 | VP-VAc (60:40) + metconazole/pyraclostrobin (2:3) | 64 | 0 |
|  |  | 32 | 0 |
|  |  | 16 | 8 |
| F-4 | VP-VAc (60:40) + epoxyconazole/pyraclostrobin (5:7) | 64 | 0 |
|  |  | 32 | 0 |
|  |  | 16 | 6 |
| C-0 | Random VP-VAc (60:40) + epoxyconazole | 16 | 9 |
|  |  | 8 | 19 |
|  |  | 4 | 73 |
| C-1 | Random VP-VAc (60:40) + metconazole | 32 | 17 |
|  |  | 16 | 50 |
|  |  | 8 | 65 |
| C-2 | Random VP-VAc (60:40) + metconazole/epoxyconazole (3:2) | 32 | 1 |
|  |  | 16 | 10 |
|  |  | 8 | 40 |
| C-3 | Random VP-VAc (60:40) + metconazole/pyraclostrobin (2:3) | 64 | 15 |
|  |  | 32 | 52 |
|  |  | 16 | 75 |
| C-4 | Random. VP-VAc (60:40) + epoxyconazole/pyraclostrobin (5:7) | 64 | 12 |
|  |  | 32 | 43 |
|  |  | 16 | 83 |

E) Crystallization Inhibitory Effect

One or more agrochemical active ingredients (epoxyconazole, metconazole and/or pyraclostrobin) and the block copolymer as in Ex. 4 were mixed in the weight ratio active ingredient:polymer 1:2 and dissolved in DMF, and the solvent was then removed in a drying cabinet. The solid solution obtained in this way was taken up with sufficient water to produce a 2% strength by weight solution, based on the polymer content. Using a light microscope, the aqueous solution was assessed after 1 hour with stirring with regard to the formation of active ingredient crystals. For comparison, the process was repeated with the comparable random VP-VAc copolymer 60/40.

The following table (column "crystals observed") shows that, in the presence of the block copolymer, the active ingredients do not crystallize out (experiments F-0 to F-4), whereas in the case of the corresponding active ingredient formulations with random copolymer (experiments C-0 to C-4), crystals were observed.

| No. | Composition | Crystals observed |
|---|---|---|
| K-1 | Without active ingredient, without polymer | n.a. |
| K-2 | VP-VAc (60:40), without active ingredient | n.a. |
| K-3 | Random VP-VAc (60:40), without active ingredient | n.a. |
| F-0 | VP-VAc (60:40) + epoxyconazole | No |
| F-1 | VP-VAc (60:40) + metconazole | No |
| F-2 | VP-VAc (60:40) + metconazole/epoxyconazole (3:2) | No |
| F-3 | VP-VAc (60:40) + metconazole/pyraclostrobin (2:3) | No |
| F-4 | VP-VAc (60:40) + epoxyconazole/pyraclostrobin (5:7) | No |
| C-0 | Random VP-VAc (60:40) + epoxyconazole | Yes |
| C-1 | Random VP-VAc (60:40) + metconazole | Yes |
| C-2 | Random VP-VAc (60:40) + metconazole/epoxyconazole (3:2) | Yes |
| C-3 | Random VP-VAc (60:40) + metconazole/pyraclostrobin (2:3) | Yes |
| C-4 | Random. VP-VAc (60:40) + epoxyconazole/pyraclostrobin (5:7) | Yes |

The invention claimed is:

1. A composition comprising at least one agrochemical active ingredient that is sparingly soluble in water, and at least one polyvinyllactam-polyvinyl acetate block copolymer, wherein the at least one agrochemical active ingredient and the at least one polyvinyllactam-polyvinyl acetate block copolymer form a solid solution in which the at least one agrochemical active ingredient is present in a molecularly dispersed form in the solid polymer matrix, wherein said block copolymer has an average molecular weight Mn of from 10,000 to 30,000 and wherein the molar ratio of polyvinyllactam to polyvinylacetate ranges from 30 to 70 to 70 to 30 wherein said polyvinyllactam block is polyvinylpyrrolidone.

2. The composition of claim 1, wherein said polyvinyllactam-polyvinyl acetate block copolymer has an A-B, A-B-A or B-A-B structure.

3. The composition of claim 1, wherein said block copolymer is water-soluble or water-dispersible.

4. The composition of claim 1, wherein said agrochemical active ingredients are selected from the group consisting of epoxiconazole, metconazole, pyraclostrobin, kresoxim-methyl and 5-chloro-7-(4-methylpiperidin-1-yl)-6-(2,4,6-trifluorophenyl)-[1,2,4]triazolo[1,5-a]pyrimidine and boscalid.

5. The composition of claim 1, wherein said agrochemical active ingredients are a mixture of agrochemical active ingredients comprising at least two different triazoles.

6. The composition of claim 5, wherein said mixture of agrochemical active ingredients comprises at least one triazole and at least one strobilurin.

7. The composition of claim 1, wherein the agrochemical active ingredient is selected from the group consisting of strobilurins, carboxamides, and azoles.

8. The composition of claim 1, wherein at least 10,000 grams of water per gram of the agrochemical active ingredient is required to dissolve the agrochemical active ingredient.

9. The composition of claim 5, wherein the mass ratio of the at least one polyvinyllactam-polyvinyl acetate block copolymer to the agrochemical active ingredient ranges from 1:2 (w/w) to 50:1 (w/w).

10. A method of preparing the composition of claim 1 comprising, mixing said agrochemical active ingredients and said polyvinyllactum-polyvinyl acetate block copolymer.

11. A method of solubilizing said agrochemical active ingredients of claim 1 comprising, mixing said agrochemical active ingredients, said polyvinyllactum-polyvinyl acetate block copolymer and water.

12. The method of claim 11, wherein at least 30 g of water is required per g of said active ingredient(s) at 20° C.

13. A method of controlling undesired insect or mite attack on plants and/or for controlling phytopathogenic fungi, wherein the fungi/insects, their habitat or the plants or ground to be protected against fungal or insect attack, or the plants, the ground on which the plants grow, or seeds thereof are treated with a composition of claim 1.

14. A method of controlling undesired plant growth, wherein the undesired plants, the ground on which the undesired plants grow, or seeds thereof are treated with a composition of claim 1.

\* \* \* \* \*